(12) United States Patent
Farazi et al.

(10) Patent No.: US 7,974,687 B1
(45) Date of Patent: Jul. 5, 2011

(54) METHODS AND SYSTEMS FOR ENHANCED ARRHYTHMIA DISCRIMINATION

(75) Inventors: Taraneh Ghaffari Farazi, San Jose, CA (US); Ruth Lyons, Glendale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 787 days.

(21) Appl. No.: 12/017,234

(22) Filed: Jan. 21, 2008

(51) Int. Cl.
*A61B 5/04* (2006.01)

(52) U.S. Cl. ......................................... 600/515; 607/5

(58) Field of Classification Search ................ 607/4–28; 600/508–519
See application file for complete search history.

(56) References Cited

U.S. PATENT DOCUMENTS

| | | | |
|---|---|---|---|
| 5,810,739 A | 9/1998 | Bornzin et al. | |
| 5,868,793 A | 2/1999 | Nitzsche et al. | |
| 5,891,170 A | 4/1999 | Nitzsche et al. | |
| 6,230,055 B1 | 5/2001 | Sun et al. | |
| 6,636,764 B1 | 10/2003 | Fain et al. | |
| 6,671,548 B1 | 12/2003 | Mouchawar et al. | |
| 6,748,269 B2 | 6/2004 | Thompson et al. | |
| 7,027,863 B1 | 4/2006 | Prutchi et al. | |
| 7,245,968 B1 | 7/2007 | Farazi et al. | |
| 7,274,961 B1 | 9/2007 | Kroll et al. | |
| 2004/0002743 A1 | 1/2004 | Park et al. | |
| 2004/0098057 A1* | 5/2004 | Pastore et al. | 607/11 |
| 2006/0116592 A1* | 6/2006 | Zhou et al. | 600/509 |
| 2006/0167364 A1 | 7/2006 | Houben | |
| 2008/0091239 A1* | 4/2008 | Johansson et al. | 607/4 |

FOREIGN PATENT DOCUMENTS

WO 0130436 A2 5/2001

* cited by examiner

*Primary Examiner* — Scott M Getzow
(74) *Attorney, Agent, or Firm* — Theresa Takeuchi; Steven M. Mitchell

(57) ABSTRACT

Embodiments of the present invention are for use with implantable cardiac devices that discriminate between ventricular tachycardia (VT) and supraventricular tachyarrhythmia (SVT). Discrimination between VT and SVT can be based on: a detected absence, presence or degree of T-wave alternans leading up to the onset of a detected tachycardia; a detected absence, presence or degree of T-wave variability leading up to the onset of the detected tachycardia; and/or a detected cardiac electrical stability leading up to the onset of the detected tachycardia.

25 Claims, 5 Drawing Sheets

METHODS AND SYSTEMS FOR ENHANCED ARRHYTHMIA DISCRIMINATION

FIELD OF THE INVENTION

Embodiments of the present invention relate to implantable cardiac devices, and methods for use therewith, that are used to discriminate between different types of arrhythmias.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atriventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias; those that result in a faster heart rate than normal are called tachyarrhythmias. Tachyarrhythmias are further classified as supraventricular tachyarrhythmias (SVTs) and ventricular tachyarrhythmia (VT). Supraventricular tachyarrhythmias (SVTs) are characterized by abnormal rhythms that may arise in the atria or the atrioventricular node (AV node). For example, a paroxysmal SVT can exhibit heart rates between approximately 140 beats per minute (bpm) and approximately 250 bpm. However, the most common SVTs are typically atrial flutter (AFI) and atrial fibrillation (AF). In addition, many SVTs involve the AV node, for example, AV nodal reentry tachycardia (AVNRT) where an electrical loop or circuit includes the AV node.

Atrial flutter (AFl) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained ventricular tachycardia can lead to ventricular fibrillation. In sustained ventricular tachycardia, consecutive impulses arise from the ventricles at a rate of 100 bpm or more. Such activity may degenerate further into disorganized electrical activity known as ventricular fibrillation (VF). In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia.

It has been common practice for an implantable cardioverter defibrillator (ICD) to monitor heart rate, or more commonly the ventricular rate, of a patient and classify the cardiac condition of the patient based on this heart rate. For example, a tachyarrhythmia may be defined as any rate in a range above a designated threshold. This range is then divided into ventricular tachycardia and ventricular fibrillation zones. The ventricular tachycardia zone may be further divided into slow ventricular tachycardia and fast ventricular tachycardia zones.

As described above, SVTs and ventricular arrhythmias may lead to ventricular rates in excess of 100 bpm. In other words, ventricular rates of SVTs can overlap with rates of tachycardias of ventricular origin. These SVTs are often well tolerated and require no intervention. Further, physically active patients can have heart rates during exercise that overlap with their tachycardia rates. Accordingly, discrimination of VT from SVT, including increased heart rates due to exercise, may require more than just knowledge of a patient's ventricular rate. In other words, using heart rate as the sole criterion to classify the cardiac condition of a patient is often not sufficient.

To improve the specificity and accuracy of arrhythmia characterization, many implantable cardiac devices (ICDs) can also examine the morphology of an intracardiac electrogram (IEGM), in addition to the heart rate. The shape of an intracardiac complex can include information on the origin and sequence of the heart's electrical activity. A normal intracardiac complex traverses the AV node and is conducted by specialized cardiac tissue throughout the ventricles. This results in a distinctive complex morphology. A tachycardia of ventricular origin often has a different morphology due to its ectopic origin and conductance through cardiac muscle tissue. As such, in addition to monitoring heart rate, some ICDs are capable of performing morphology discrimination to classify the cardiac condition of the patient. For example, a template based on the morphology of a "known" signal can be stored in the ICD. The "known" signal can be, for example, a signal collected during a period where a patient is known to exhibit a normal sinus rhythm. By comparing the morphology characteristics (e.g., number, amplitude, sequence and/or polarity of waveform peaks, as well as the area of the peaks) of an arrhythmia to the template, the ICD can calculate the match (or lack thereof) between the waveforms. For a further description of morphology discrimination, refer to U.S. Pat. No. 5,240,009 (Williams), entitled "Medical Device with Morphology Discrimination" and to U.S. Pat. No. 5,779,645 (Olson et al.), entitled "System and Method for Waveform Morphology Comparison," which patents are hereby incorporated by reference. These are just a few example of morphology discriminator algorithms and parameters, which are not intended to be limiting.

Sudden onset and interval stability (also know as rate stability), are examples of other factors that can be monitored to improve the specificity of arrhythmia characterization. Also, the relationship between ventricular rate (V) and atrial rate (A) can be used to characterize an arrhythmia. For example, this can be part of a rate branch algorithm, which, depending on V and A, may follow one of three branches: a V<A rate branch; a V=A (within a specified tolerance) rate branch; and a V>A rate branch. If V<A, then morphology discrimination and/or interval stability may be available to distinguish VT from AF or AFl. If A and V are essentially the same (within a certain tolerance), then morphology discrimination and/or sudden onset may be available to distinguish VT from sinus tachycardia. If V>A, then an arrhythmia may be characterized as VT. Also, specific branches can be turned on or off. For example, if V is greater than the tachycardia threshold but essentially the same as A, and the V=A branch is turned off, then the algorithm can cause the V>A branch to be followed, and the arrhythmia may be classified as VT. Additional details of an exemplary rate branch algorithm are provided in U.S. Pat. No. 6,636,746 (Fain et al.), entitled "Safety Backup in Arrhythmia Discrimination Algorithm," which is incorporated herein by reference. Also, atrioventricular association (AVA) can also be used to distinguish AFl from VT. In an exemplary (AVA) algorithm, the AV interval is measured from each ventricular sensed event to its preceding atrial event and an AVA Delta is then calculated as the difference between the second longest AV interval and the second shortest AV interval in a recent group of intervals. If the measured AVA Delta is less than a programmable AVA threshold parameter, the AV intervals are considered stable, which is indicative of SVT. If the measured AVA Delta is greater than or equal to a programmable AVA threshold parameter, the AV intervals are considered unstable, which is indicative of VT. More generally, the relative rate of the atria and ventricles and/or the timing relationship between atrial and ventricular events can be considered.

Typically an ICD is programmed to provide a therapy in response to an arrhythmia being detected, where the type of therapy corresponds to the type of arrhythmia that the ICD believes it has detected. For example, VT may be treated with a therapy consisting of low-energy pacing pulses designed to capture the ventricles. This therapy is referred to as ventricular Anti-Tachycardia Pacing therapy (ATP). VT may also be treated with relatively low energy, synchronized cardioversion shocks. VF, on the other hand, is typically treated more aggressively with high energy shocks. SVT may not be treated, or may be treated using atrial ATP or atrial defibrillation. Quite often, SVT is treated using medication, or ablation.

Despite the numerous arrhythmia discrimination techniques that exist, examples of which were provided above, delivery of inappropriate shocks remains a major problem with ICDs today. Accordingly, there is still a need for new, and preferably improved, arrhythmia discrimination techniques.

SUMMARY

Embodiments of the present invention are directed to techniques for use with implantable cardiac devices to discriminate between ventricular tachycardia (VT) and supraventricular tachyarrhythmia (SVT). Embodiments of the present invention are also directed to implantable cardiac devices and systems that are configured to implement such techniques.

In accordance with specific embodiments, an absence, presence or degree of T-wave alternans is detected in a portion of an IEGM signal indicative of cardiac activity leading up to the onset of a detected tachycardia. Discriminating between VT and SVT is then based on the detected absence, presence or degree of T-wave alternans in the portion of the IEGM signal. If T-wave alternans were present or a degree of T-wave alternans exceeded a specified threshold, it is determined that the portion of the IEGM signal is indicative of VT. If T-wave alternans were absent or a degree of T-wave alternans did not exceed a specified threshold, it is determined that the portion of the IEGM signal is indicative of SVT. To discriminate between VT and SVT, such T-wave alternans analysis can be used as the sole arrhythmia discrimination qualifier, or together with other discrimination qualifiers, such as morphology, sudden onset and/or interval stability. A first type of cardiac therapy can be delivered if it is determined that the detected tachycardia is VT. A second type of cardiac therapy, or no cardiac therapy, can be delivered if it is determined that the detected tachycardia is SVT.

There can be a substantially continual monitoring for a tachycardia, and a substantially continual monitoring for an absence, presence or degree of T-wave alternans while monitoring for a tachycardia. This way, when a tachycardia is detected, there can be a substantially immediate determination of the absence, presence or degree of T-wave alternans in the portion of the IEGM signal indicative of cardiac activity leading up to the onset of the detected tachycardia.

In other embodiments, a portion of an IEGM is repeatedly stored in a buffer. When a tachycardia is detected, contents of the buffer are froze so that the contents of the buffer includes the portion of the IEGM signal indicative of cardiac activity leading up to the onset of the detected tachycardia. Then, based on the contents of the buffer, there can be a determination of the presence, absence or degree of T-wave alternans in the portion of the IEGM signal indicative of cardiac activity leading up to the onset of the detected tachycardia.

In other embodiments, an absence, presence or degree of T-wave variability is detected in a portion of an IEGM signal indicative of cardiac activity leading up to the onset of a detected tachycardia. Discriminating between VT and SVT is then based on the detected absence, presence or degree of T-wave variability in the portion of the IEGM. If T-wave variability was present or a degree of T-wave variability exceeded a specified threshold, it is determined that the portion of the IEGM signal is indicative of VT. If T-wave variability was absent or a degree of T-wave variability did not exceed a specified threshold, it is determined that the portion of the IEGM signal is indicative of SVT.

In certain embodiments, the cardiac electrical stability leading up to the onset of a detected tachycardia is used to discriminate between VT and SVT. If the cardiac electrical stability leading up to the onset of a detected tachycardia is determined to be instable, it is determined that the cardiac electrical stability is indicative of VT. If the cardiac electrical stability leading up to the onset of a detected tachycardia is determined to be stable, then it is determined that the cardiac electrical stability is indicative of SVT.

This summary is not intended to be a complete description of the invention. Other features and advantages of the invention will appear from the following description in which the preferred embodiments have been set forth in detail, in conjunction with the accompanying drawings and claims.

DETAILED DESCRIPTION OF PREFERRED EMBODIMENTS

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed systems and methods, which are for use in discriminating between different types of arrhythmias, are generally intended for use with an implantable cardiac device capable of detecting and treating arrhythmias. An exemplary implantable cardiac device will thus be described in conjunction with FIGS. 1 and 2, in which embodiments of the present invention described herein could be implemented. It is recognized, however, that numerous variations of such a device exist in which the methods could be implemented.

Figure 1:
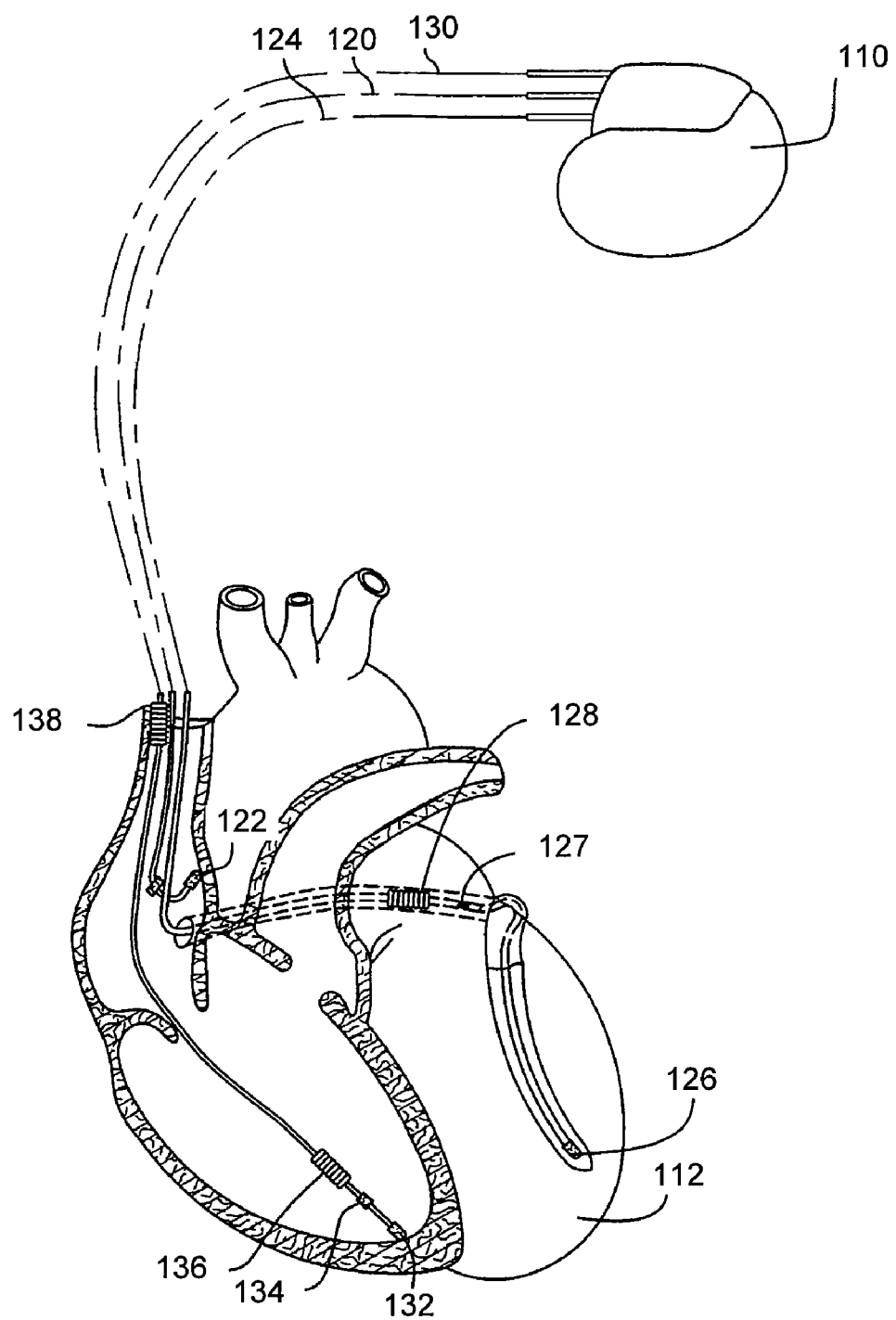
FIG. 1 is a simplified, partly cutaway view illustrating an implantable stimulation device in electrical communication with at least three leads implanted into a patient's heart for delivering multi-chamber stimulation and shock therapy.

Referring to FIG. 1, an exemplary implantable device 110 (also referred to as a pacing device, a pacing apparatus, a cardiac stimulation device, or simply a device) is in electrical communication with a patient's heart 112 by way of three leads, 120, 124 and 130, suitable for delivering multi-chamber stimulation. Preferably, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
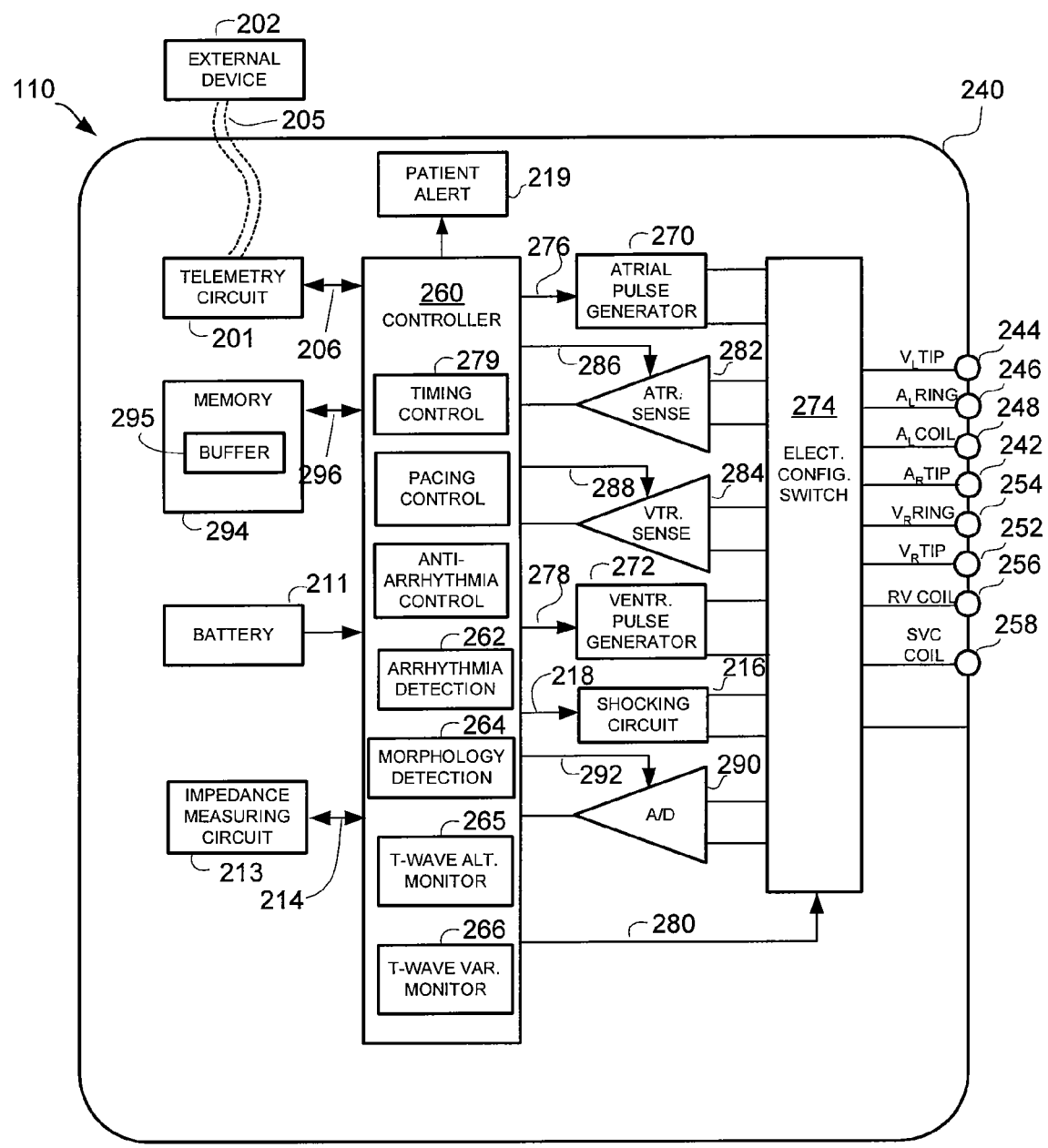
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 includes an arrhythmia detector 262 and a morphology detector 264, that utilizes the atrial and ventricular sensing circuits, 282 and 284, to sense cardiac signals to determine whether a rhythm is physiologic or pathologic. The morphology detector 264 can, e.g., assess characteristics such as amplitude, area under curves, polarity, and shape, of detected cardiac rhythms.

The arrhythmia detector 264 can analyze the timing intervals between sensed events (e.g., P-waves, R-waves, and depolarization signals associated with fibrillation) and compare them to predefined rate zone limits (e.g., bradycardia, normal, low rate VT, high rate VT, and fibrillation rate zones), and various other characteristics such as morphology (as determined by the morphology detector 264) and/or sudden onset, stability, physiologic sensors, etc., in order to classify an arrhythmia, and thus, determine the type of remedial therapy that is needed (e.g., bradycardia pacing, anti-tachycardia pacing, cardioversion shocks or defibrillation shocks).

The arrhythmia detector 262 and/or morphology detector 264 can be implemented within the microcontroller 260, as shown in FIG. 2. Thus, the detectors 262 and/or 264 can be implemented by software, firmware, or combinations thereof. It is also possible that all, or portions, of the arrhythmia detector 262 and/or morphology detector 264 can be implemented using hardware. Further, it is also possible that all, or portions, of the detectors 262 and/or 264 can be implemented separate from the microcontroller 260. It is also possible that the features of the arrhythmia detector and morphology detector be incorporated into a single detector. The arrhythmia detector 262 can also receive information from a T-wave alternans monitor 265 and/or a T-wave variability monitor 266, where the information can be used the classifying an arrhythmia, as will be described in more detail below.

Exemplary types of arrhythmias that the arrhythmia detector 262 can detect include, but are not limited to, SVT (e.g., AF), VT and VF. A tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). VTs begins in the ventricles. Some are harmless, but others are life threatening in that they can quickly deteriorate to VF. Some VTs are harmful even before they deteriorate into VF, or even if they don't deteriorate to VF (e.g., they can cause hemodynamic deterioration that can cause collapse).

VF is a very fast (e.g., over 200 beats per minute) and chaotic heart rate in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF typically quickly becomes more erratic, often resulting in sudden cardiac arrest. This arrhythmia should be corrected immediately via a shock from an external defibrillator or an implantable cardioverter defibrillator (ICD). The defibrillator stops the chaotic electrical activity and restores normal heart rhythm. These are just a few examples of the types of arrhythmias that the arrhythmia detector 262 can detect. One of ordinary skill in the art will appreciate that other types of arrhythmias can be detected, and information for such other types of arrhythmias can be stored.

The device 110 is also shown as including a T-wave alternans monitor 265 and a T-wave variability monitor 266. The T-wave alternans monitor 265 and/or the T-wave variability monitor 266 can be implemented within the microcontroller 260, as shown in FIG. 2. Thus, the monitors 265 and/or 266 can be implemented by software, firmware, or combinations thereof. It is also possible that all, or portions, of the monitors 265 and/or 266 can be implemented using hardware. Further, it is also possible that all, or portions, of the monitors 265 and/or 266 can be implemented separate from the microcontroller 260. It is also possible that the features of the T-wave alternans monitor 265 and the T-wave variability monitor 266 can be incorporated into a single monitor, which may or may not be part of the arrhythmia detector 262. The T-wave alternans monitor 265 can monitor for the absence, presence and/or magnitude of T-wave alternans. The T-wave variability monitor 266 can monitor for the absence, presence and/or magnitude of T-wave variability. Exemplary details of T-wave alternans and T-wave variability monitoring are provided below.

In accordance with specific embodiments of the present invention, the implantable device 110 can store, in memory 294, IEGM signal data corresponding to the period immediately prior to, during and subsequent to a detected arrhythmia. The implantable device can also store data that identifies the type of arrhythmia, the time of the arrhythmia (e.g., a time stamp), the duration of the arrhythmia, as well as any other type of information that a caregiver may deem useful. U.S. Pat. No. 4,295,474 (Fischell) and U.S. Pat. No. 5,732,708 (Nau et al.), each of which is incorporated herein by reference, provide exemplary additional details of the types of data that can be stored in response to the detection of an arrhythmia (and other cardiac events), and how such data can be efficiently and effectively stored.

Still referring to FIG. 2, cardiac signals are also applied to the inputs of an analog-to-digital (A/D) data acquisition system 290. The data acquisition system 290 is configured to acquire intracardiac electrogram (IEGM) signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130, and/or any other lead, through the switch 274 to sample cardiac signals across any pair of desired electrodes. In specific embodiments, the data acquisition system 290 may be used to acquire IEGM signals for the analysis.

In accordance with specific embodiments of the present invention, the memory 294 includes a buffer 295 that continually stores a portion of an acquired IEGM signal, e.g., that last 30 seconds, last minute, last 5 minutes, etc. of a wideband IEGM signal. Alternatively, such a buffer can be part of the on-chip memory of the controller 260. It's also possible that there be a buffer dedicated to storing a recent portion of an IEGM signal. Such a dedicated buffer can be receive, e.g., the output of the data acquisition system 290. In accordance with specific embodiments of the present invention, such a buffer, regardless of where it is located, enables the implantable system to analyze a portion of an IEGM signal that leads up to the onset of a tachycardia, as will be described in further detail below. Alternatively, T-wave metrics can be determined in real or near real time and such metrics can be stored in the buffer. In this manner, T-wave alternans and/or T-wave variability analysis can be based on the T-wave metrics stored in the buffer.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy.

The operating parameters of the implantable device 110, including arrhythmia discrimination parameters and algorithms, may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected. Certain embodiments of the present invention, as will be appreciated from the discussion further below, can be used to extend the life a the battery 211 by reducing the quantity of high voltage shocks delivered.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

Because the implantable device 110 may operate as an implantable cardioverter defibrillator device, it should detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, e.g., selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode). Use of additional and/or alternative electrodes is also possible, as would be appreciated by one of ordinary skill in the art.

The above described implantable device 110 was described as an exemplary device. One or ordinary skill in the art would understand that embodiments of the present invention can be used with alternative types of implantable devices. Accordingly, embodiments of the present invention should not be limited to use only with the above described device.

Figure 3:
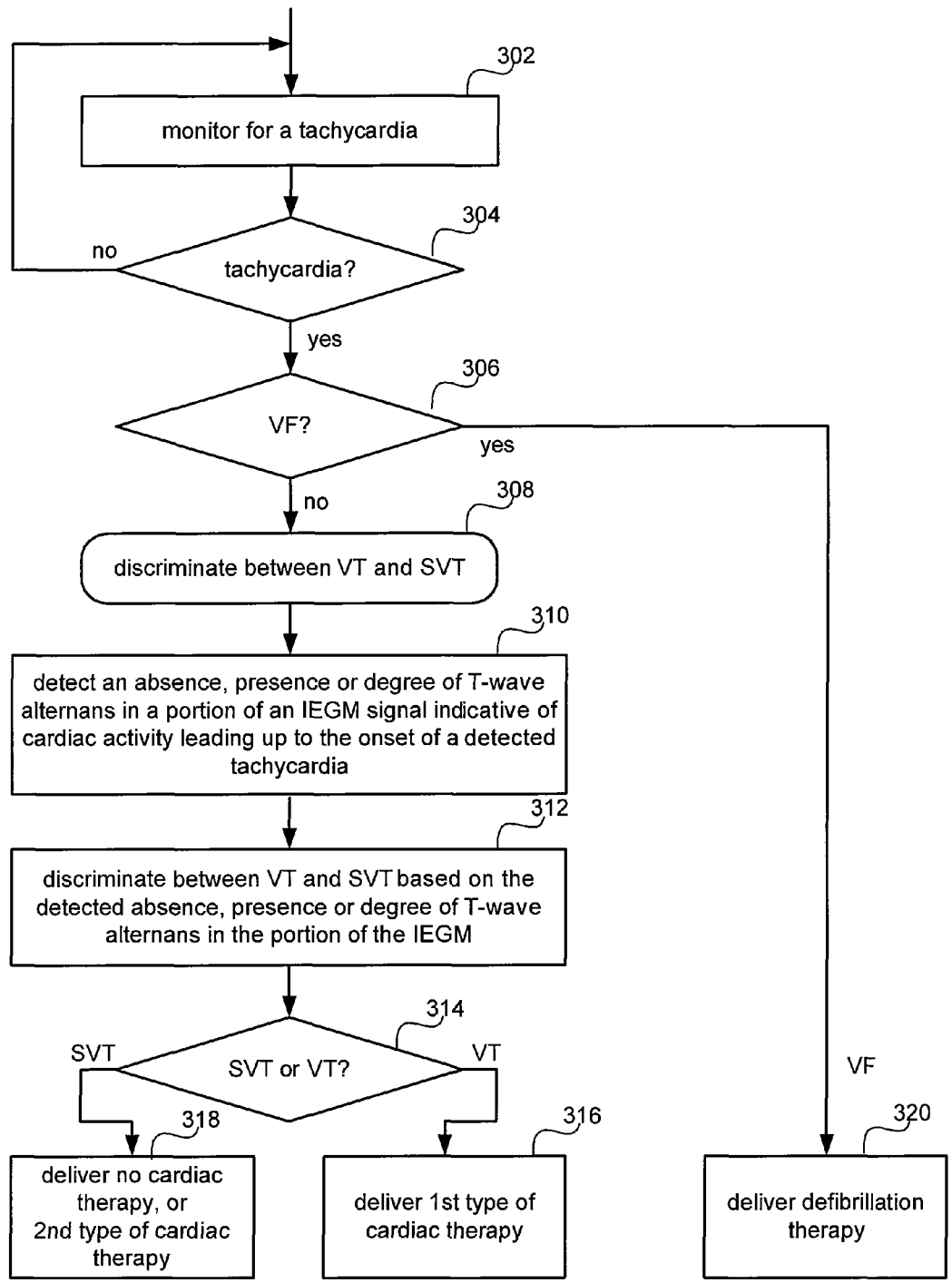
FIG. 3 is a high level flow diagram that is used to summarize specific embodiments of the present invention that relate discriminating between VT and SVT based on a detected absence, presence or degree of T-wave alternans in a portion of an IEGM leading up to the onset of a tachycardia.
Figure 4:
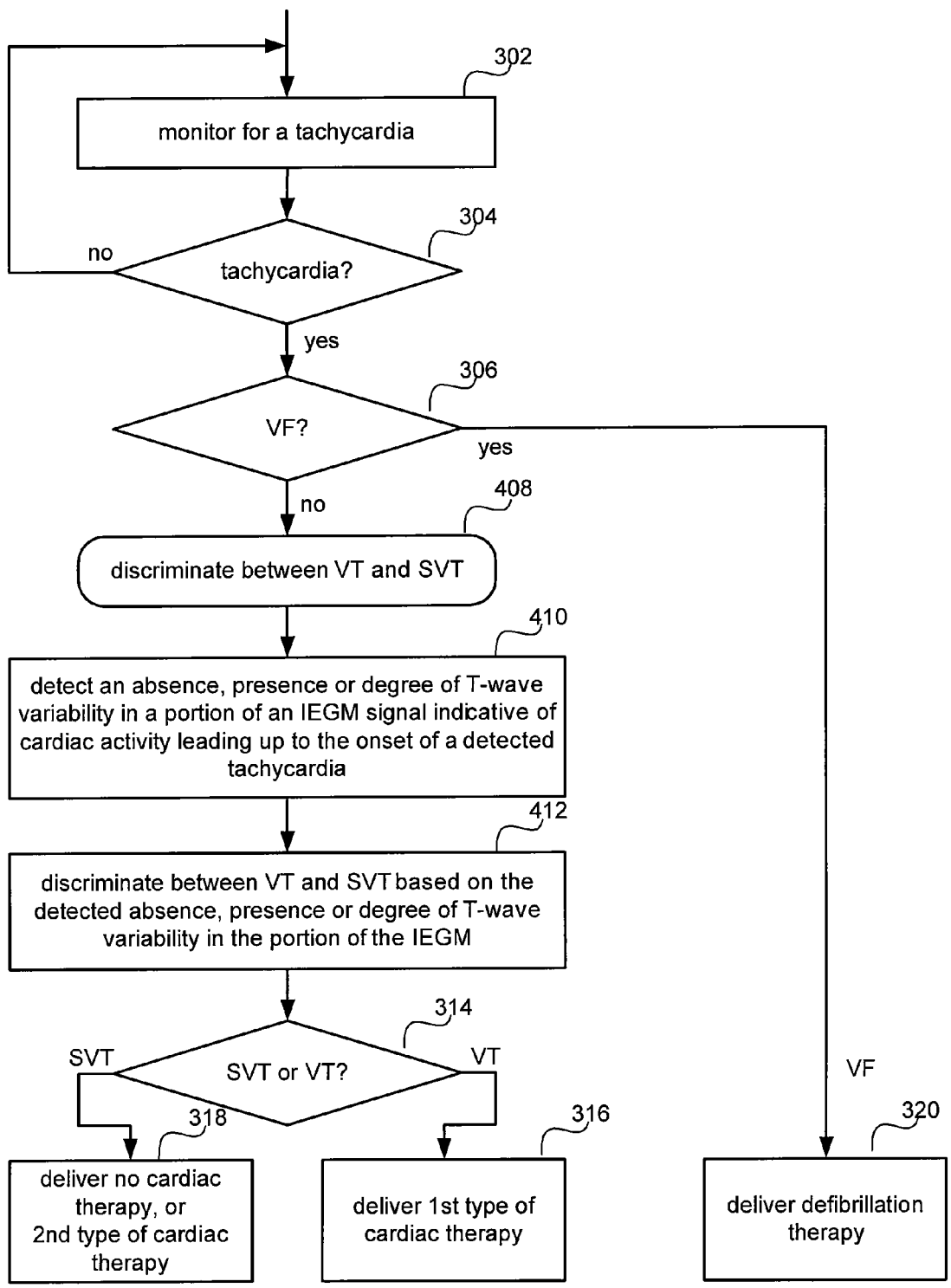
FIG. 4 is a high level flow diagram that is used to summarize specific embodiments of the present invention that relate discriminating between VT and SVT based on a detected absence, presence or degree of T-wave variability in a portion of an IEGM leading up to the onset of a tachycardia.
Figure 5:
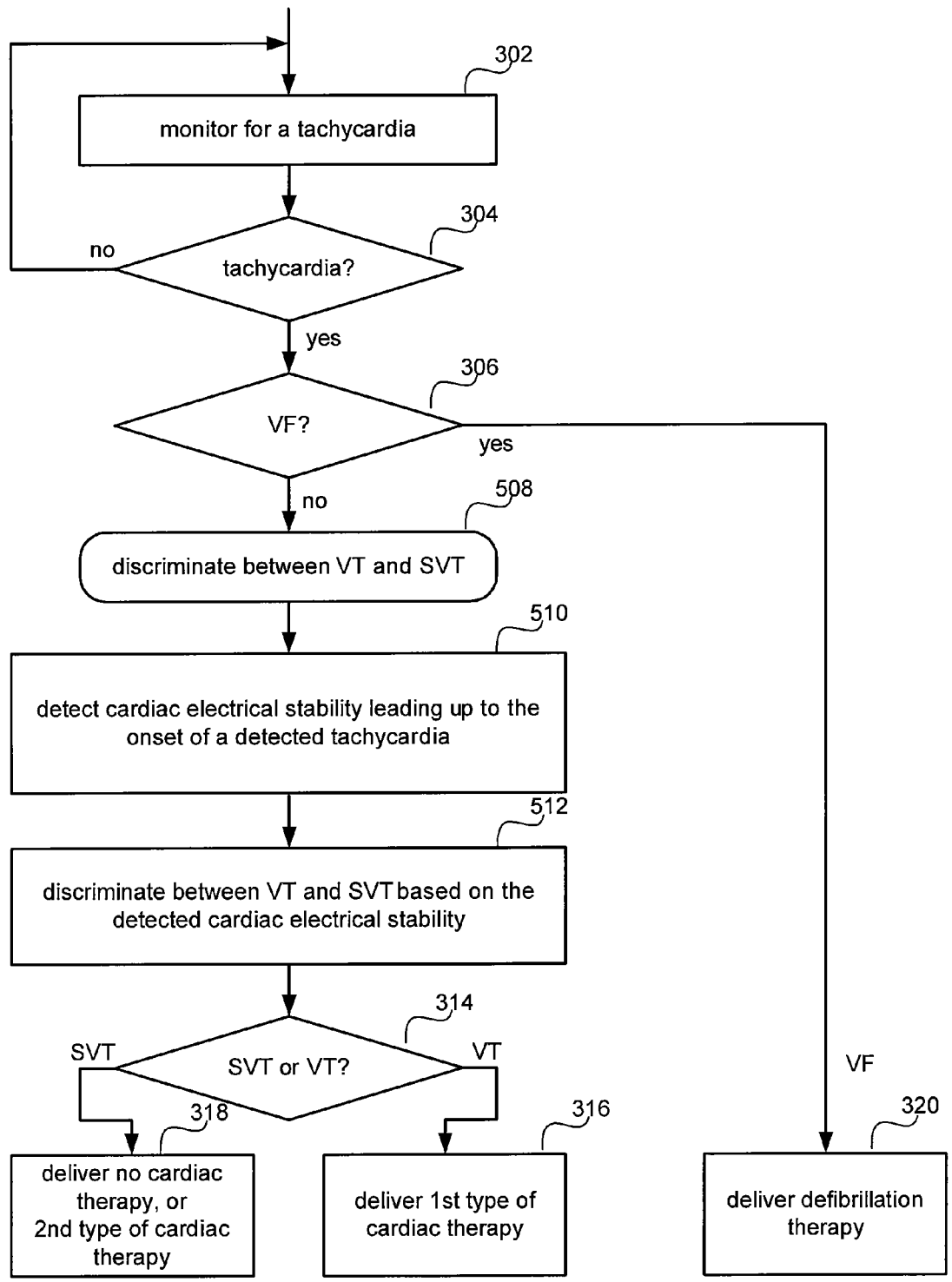
FIG. 5 is a high level flow diagram that is used to summarize specific embodiments of the present invention that relate discriminating between VT and SVT based on a detected cardiac electrical stability leading up to the onset of a tachycardia.

Specific embodiments of the present invention shall now be summarized with reference to the high level flow diagrams of FIGS. 3-5. Such embodiments can be used with an implantable cardiac device that discriminates between ventricular tachycardia (VT) and supraventricular tachyarrhythmia (SVT).

FIG. 3 is a high level flow diagram that is used to summarize specific embodiments of the present invention, which are used to discriminate between VT and SVT, as indicated by block 308. Referring to the top of FIG. 3, monitoring for a tachycardia occurs at step 302. This can include obtaining one or more intracardiac electrogram (IEGM) signals, so that the IEGM signal(s) can be monitored to detect tachycardias, as well at to monitor for T-wave alternans. Exemplary leads and electrodes that can be used to obtain an IEGM were discussed above with reference to FIGS. 1 and 2. It is well know how to obtain an IEGM, thus additional details of how to obtain an IEGM are not necessary.

As mentioned above, a tachycardia is any cardiac arrhythmia characterized by a rapid rate, e.g., usually over 100 beats per minute. Tachycardias may be normal, as in the case of a sinus tachycardia induced by exercise, or may indicate an abnormal rhythm, e.g., VT or VF. A tachycardia can be monitored for by monitoring ventricular and/or atrial cycle lengths and/or rates, and comparing such metric(s) to an appropriate threshold(s). For example, a tachycardia can be detected if a ventricular cycle length (CL) falls below a VT CL threshold, or a ventricular rate exceeds and VT rate threshold. Other tachycardia detection techniques are also possible, and within the scope of the present invention.

As shown at step 304, step 302 is repeated until a tachycardia is detected. When a tachycardia is detected, there can be an immediate discrimination between VT and SVT, or preferably, there is first a determination of whether the tachycardia is VF, as shown at step 306. VF detection can occur, e.g., when the ventricular rate is determined to exceed a VF rate threshold. Other VF detection techniques are also possible, and within the scope of the present invention. If VF is diagnosed, then defibrillation therapy can be delivered, as indicated at step 320, in an attempt to convert the VF to a normal sinus rhythm. Defibrillation therapy can include, e.g., delivery of defibrillation shocks, but is not limited thereto.

If it is determined at step 306 that the tachycardia is not VF, then there can be a determination of whether the tachycardia is either VT or SVT, as indicated by block 308. In other words, arrhythmia discrimination can take place, details of which are explained with reference to steps 310 and 312.

At step 310, there is a determination of an absence, presence or degree of T-wave alternans in a portion of an IEGM signal indicative of cardiac activity leading up to the onset of a detected tachycardia. More specifically, there can be a binary determination, at step 310, of whether T-wave alternans are present or absent (i.e., not present). This determination can take place by determining a magnitude of alternation of T-waves (in a portion of an IEGM signal indicative of cardiac activity leading up to the onset of a detected tachycardia), and comparing the determined magnitude to a threshold (e.g., a baseline). If the threshold is not exceeded, then there can be a determination that T-wave alternans were absent. If the threshold is reached or exceeded, then there can be a determination that T-wave alternans were present. The extent of the length of the IEGM signal (indicative of cardiac activity leading up to the onset of a detected tachycardia) can be programmed as desired, e.g., to be 30 second, 1 minute, 90 seconds, 2 minutes, 3 minutes, etc.

Alternatively, at step 310, a degree of T-wave alternans can be determined, meaning that there can be various levels of T-wave alternans, and that more than a binary decision occurs. For example, there can be two, three or more (e.g., infinite) possible degrees of T-wave alternans. Additional details of how to determine the absence, presence or degree of T-wave alternans from an IEGM signals are discussed in more detail below.

At step 312, there is a discrimination between VT and SVT based on the results of step 310, and more specifically, based on the detected absence, presence or degree of T-wave alternans in the portion of the IEGM signal indicative of cardiac activity leading up to the onset of the detected tachycardia. As will be appreciated from the discussion below, the phrase "base on", unless stated otherwise, means based at least in part on, meaning that when a determination is "based on" a factor, other factors can also be used in making the determination.

It is believed that the presence of T-wave alternans prior to the onset of a tachycardia is indicative of VT, where the absence of T-wave alternans prior to the onset of a tachycardia is indicative of SVT. Additionally, it is believed that the degree of T-wave alternans (if that is what is being monitored) will increase prior to the onset of VT, but will stay relatively the same prior to the onset of SVT. Accordingly, in accordance with specific embodiments of the present invention, T-wave alternans analysis is used in the discrimination between VT and SVT.

More specifically, at step 312, if T-wave alternans were present or a degree of T-wave alternans exceeded a specified threshold, there can be a determination that the portion of the IEGM signal is indicative of VT. In contrast, if T-wave alternans were absent or a degree of T-wave alternans did not exceed a specified threshold, there can be a determination at step 312 that the portion of the IEGM signal is indicative of SVT.

T-wave alternans analysis can be used as the sole arrhythmia discrimination qualifier, are more likely, as one of a few or many discrimination qualifiers, some of which were discussed above, including morphology, sudden onset, and interval stability (also known as rate stability). In other words, the above described T-wave alternans analysis can be used to independently discriminate between VT and SVT, or can be used together with other techniques for discrimination between VT and SVT. For example, the above described embodiments can be used to supplement (e.g., to increase the confidence level of) arrhythmia discrimination performed using some other technique(s), including but not limited to interval stability, sudden onset and morphology discrimination techniques. Alternatively, some other technique(s) can be used to supplement the arrhythmia discrimination performed using the T-wave alternans analysis described above. It is also possible that the T-wave alternans analysis be used in one or more branch of rate branch algorithm, examples of which are described above. Some exemplary details of interval stability, sudden onset and morphology discrimination techniques are provided below, for completeness.

Interval stability discrimination techniques can be used to assist in discriminating between episodes of VT and episodes of AF (which is a type of SVT), because VTs are typically very stable, whereas the rhythm from one beat to the next during AF is typically less stable (i.e., more irregular). Depending upon the algorithm used, the value of an interval stability parameter can be a value of stability (also referred to as variability), which can be defined by a range, variance, standard deviation, or the like. For example, if a cardiac rhythm exceeds the tachycardia detection rate parameter, and the stability is within that defined by the stability discriminator value (e.g., the standard deviation of the rhythm is less than the standard deviation discriminator value), then the implantable cardiac device can interpret that as an indicator of VT. Interval stability is sometime referred to as rate stability, because rate and interval are simply inverses of one another.

Sudden onset discrimination techniques can be used to assist in distinguishing between VT and a sinus tachycardia type SVT that is due to exercise (e.g., walking up a flight of stairs). Typically, a sinus tachycardia has a gradual rate of onset, while VT has a more abrupt onset. Such onset can be measured, e.g., by determining a difference between the average RR interval for N beats prior to a first beat that exceeds the tachycardia detection rate, and the average RR interval for N beats following the first beat that exceeds the tachycardia detection rate (e.g., N can be 1 or more). Accordingly, the value of a sudden onset discriminator parameter can be specified in milliseconds. Where the sudden onset discriminator value is exceeded, the implantable cardiac device interprets that as an indicator of VT. Where a sudden onset discriminator value is not exceeded, the implantable cardiac device interprets that as an indicator of SVT.

Morphology discrimination techniques can be also be used to assist in discrimination between VT and SVT, because SVTs originate in the atria and follow the normal conduction pathway to the ventricles (typically via the AV node), causing the morphology (shape) of the resulting QRS complexes to look similar to the morphology of a QRS complex of a normal sinus rhythm. In contrast, VT arises from outside normal conduction system, causing the morphology of the resulting QRS complex to be less similar to that of a normal sinus rhythm. To perform such morphology comparisons, a template QRS complex is typically obtained and stored when a patient is known to have a normal sinus rhythm. Thereafter, the template QRS complex can be compared to present QRS complexes in real or near real time, to determine a level of similarity. A morphology discriminator parameter can specify, e.g., the level of similarity below which a rhythm is classified as indicative of VT, and above which the rhythm is classified as indicative of SVT. For a more specific example, a morphology algorithm can measure attributes such as the number of peaks, amplitude of peaks, polarity, and area under curves of a QRS complex, and compares such complexes to the template QRS complex to generate a percent match between 0 and 100%. For this example, a morphology discriminator parameter can specify the percentage match, above which the implantable cardiac device interprets as indicative of SVT, and below which the device interprets as indicative of VT.

Still referring to FIG. 3, the result of step 312 is either a VT diagnosis, or an SVT diagnosis, which as described below, is used to select how and/or whether to treat the tachycardia. A VT diagnosis means that tachycardia is classified as VT, and an SVT diagnosis means that the tachycardia is classified as SVT.

If the tachycardia is classified as VT, then a first type of cardiac therapy can be delivered, as shown at step 316. The first type of cardiac therapy can include ventricular antitachycardia pacing (ATP) and/or cardioversion shocks, but is not limited thereto.

If the tachycardia is classified as SVT, then a second type of cardiac therapy, or no cardiac therapy, can be delivered, as shown at step 318. The second type of cardiac therapy can include, e.g., atrial ATP or atrial defibrillation.

In accordance with specific embodiments, the implantable system can substantially continually monitoring for a tachycardia, and substantially continually monitoring for an absence, presence or degree of T-wave alternans while monitoring for a tachycardia. This way, when a tachycardia is detected, there can be a substantially immediate determination of the absence, presence or degree of T-wave alternans in a portion of an IEGM signal indicative of cardiac activity leading up to the onset of the detected tachycardia.

In an alternative embodiment, the detection of a tachycardia by the implantable system can trigger the determination of the absence, presence or degree of T-wave alternans. More specifically, a portion of an IEGM can be repeatedly stored in a buffer (e.g., buffer 295). Then, when a tachycardia is detected, the contents of the buffer can be froze, so that the contents of the buffer includes a portion of the IEGM signal indicative of cardiac activity leading up to the onset of the detected tachycardia. The implantable system can then determine, based on the contents of the buffer, the presence, absence or degree of T-wave alternans in the portion of the IEGM signal indicative of cardiac activity leading up to the onset of the detected tachycardia. Another way that the implantable system can use a buffer to determine the presence, absence or degree of T-wave alternans leading up to the onset of the detected tachycardia is as follows. T-wave metrics can be determined in real or near real time, and such metrics can be stored in a buffer. Then, when a tachycardia is detected, the contents of the buffer can be froze, so that the contents of the buffer includes T-wave metrics corresponding to cardiac activity leading up to the onset of the detected tachycardia (rather than the buffer storing raw IEGM data). The implantable system can then determine, based on the contents of the buffer, the presence, absence or degree of T-wave alternans leading up to the onset of the detected tachycardia.

To monitor for T-wave alternans, T-wave metrics can be measured to determine whether alternations in T-waves exist, and to what extent. Below are some example of how T-wave alternans can be detected. However, it is noted that embodiments of the present invention should not be limited to the specific techniques described.

The term T-wave as used herein may refer to a portion of the ventricular QRS-T-wave complex that includes the T-wave and/or the QRS-T segment. The alternating feature or metric of T-wave alternans can be detected by examination, for example, of the QT interval, T-wave width, T-wave amplitude (i.e., peak-to-peak) or morphology. Other exemplary T-wave metrics, that can be used for T-wave alternans analysis, include, but are not limited to: maximum amplitude of T-wave, minimum amplitude of T-wave, location of maximum amplitude of T-wave, location of minimum amplitude of T-wave, area under T-wave, slope of T-wave, T-wave amplitude dispersion, T-wave centroid, QT interval, corrected QT interval, amplitude of ST segment, T-wave frequency content, T-wave frequency spread, and QT max–QT end. Whatever the designated T-wave metric of the intracardiac electrogram, T-wave alternans refers to an alternating pattern of the wave that can be designated "ABABAB . . . " where A represents every other cycle and B represents every other alternate cycle. Such a pattern is often referred to as a two beat alternans pattern, or simply an AB pattern. Electrical alternans may also refer to an alternating pattern of the wave that can be designated "ABCABC . . . ", or an alternating pattern of the wave that can be designated "ABCDAB CD . . . ". The "ABCABC . . . " pattern is a three beat alternans pattern, which can be simply referred to as an ABC pattern, and the "ABCDABCD . . . " pattern is a four beat alternans pattern, which can be referred to as an ABCD pattern.

One way to detect the presence of an AB alternans pattern is to measure T-wave metrics for a plurality of consecutive beats, and then line up all the T-wave metrics of odd beats, and line up all the T-wave metrics of even beats. Ensemble averaging (or some other averaging) can then be performed to produce one or more average "odd" T-wave metric and one or more average "even" T-wave metric. A magnitude of alternation can then be determined by determining a difference between an average "odd" T-wave metric and a corresponding average "even" T-wave metric. This difference (i.e., magnitude of alternation) can be compared to a threshold to determine if T-wave alternans are present. If the difference is less than the threshold, then it can be determined that T-wave alternans are not present. If the difference (i.e., the magnitude of alternation) is greater than the threshold, then it can be determined that the T-wave alternans are present. It is also possible to have multiple thresholds such that in addition to determining whether T-wave alternans are present, changes in magnitudes of alternations can be determined. This can be used, e.g., to determine a degree of the T-wave alternans, which are indicative of myocardial electrical stability. In other words, a degree of the T-wave alternans (or more generally, magnitudes of alternation) can be determined. This type of algorithm can also be modified to look for other (e.g., three of four beat) alternans patterns.

Alternatively, the variation in T-wave amplitude of successive "odd" T-waves and "even" T-waves can be measured in a sliding window of an IGEM. The amount of T-wave variation between the odd and even T-waves can be determined. A third measure that determines the statistical significance of the difference in T-wave variations as compared to a baseline can be used to determine the presence, degree, or absence of T-wave alternans, and more generally, the electrical stability of the myocardium.

Another option would be to determine, for each pair of odd/even beats, the difference between T-wave amplitudes of the odd and even beats. Assuming such differences (which are examples of magnitudes of alternation) are determined for each of 50 separate pairs of beats, then the differences of the 50 pairs can be averaged to produce an average difference, and the absence, presence and/or degree of T-wave alternans can then be determined from the average difference.

As mentioned above, not all alternans patterns are two beat patterns. Rather, there can be three beat, four beat, etc. alternans patterns. For example, a four beat alternans (ABCD) pattern can be searched for in the following manner. Assume that 200 consecutive beats are divided into 50 separate 4 beat sets. For each 4 beat set, there can be a determination of the difference between T-wave amplitudes of the 1st and 2nd beats, the 2nd and 3rd beats, and the 3rd and 4th beats, resulting in three differences for each 4 beat set (i.e., a first difference between the metrics for 1st and 2nd beats, a second difference between the metrics for the 2nd and 3rd beats, and a third difference between the metrics for the 3rd and 4th beats). Assuming such differences (which are examples of magnitudes of alternation) are determined for each of 50 separate 4 beat sets, then the first difference of each of the 50 sets can be averaged to produce an average first difference, the second difference of each of the 50 sets can be averaged to produce an average second difference, and the third difference of each of the 50 sets can be average to produce an average third difference. The absence, presence and/or degree of T-wave alternans can then be determined from the average first difference, the average second difference and the average third difference.

Further algorithms rely of frequency domain analysis for detecting electrical alternans. Exemplary further systems and methods for detecting T-wave alternans, and more generally, monitoring myocardial electrical stability, are provided in the following commonly assigned applications, which are both incorporated herein by reference: U.S. patent application Ser. No. 11/354,699, entitled "Time Domain Monitoring of Myocardial Electrical Stability," and U.S. patent application Ser. No. 11/354,732, entitled "Frequency Domain Monitoring of Myocardial Electrical Stability," both of which were filed Feb. 14, 2006.

These are just a few examples of the ways in which the presence, the absence and/or the degree of T-wave alternans can be detected, or more generally, that myocardial electrical stability can be monitored. One of ordinary skill in the art will appreciate that many other different techniques can be used, while still being within the spirit and scope of the present invention.

Instead of, or in addition to using T-wave alternans analysis to discriminate between VT and SVT, T-wave variability analysis can be used, as will now be described with reference to the high level flow diagram of FIG. 4. More specifically, FIG. 4 is a high level flow diagram that is used to summarize specific embodiments of the present invention that relate discriminating between VT and SVT based on the detected absence, presence or degree of T-wave variability in a portion of an IEGM leading up to the onset of a tachycardia. Steps 302-306 and 314-320 in FIG. 4 are the same as those steps in FIG. 3, and thus those steps need not be discussed again. Block 408 is numbered different than block 308, to indicate that a different technique for discriminating between VT and SVT is being used at step 408, i.e., one based on T-wave variability.

Referring to FIG. 4, at step 410, there is a determination of an absence, presence or degree of T-wave variability in a portion of an IEGM signal indicative of cardiac activity leading up to the onset of a detected tachycardia. More specifically, there can be a binary determination, at step 410, of whether T-wave variability is present or absent (i.e., not present). This determination can take place by determining a magnitude of variability of T-waves (in a portion of an IEGM signal indicative of cardiac activity leading up to the onset of a detected tachycardia), and comparing the determined magnitude to a threshold (e.g., a baseline). If the threshold is not exceeded, then there can be a determination that T-wave variability was absent. If the threshold is reached or exceeded, then there can be a determination that T-wave variability was present. The extent of the length of the IEGM signal (indicative of cardiac activity leading up to the onset of a detected tachycardia) can be programmed as desired, e.g., to be 30 second, 1 minute, 90 seconds, 2 minutes, 3 minutes, etc.

Alternatively, at step 410, a degree of T-wave variability can be determined, meaning that there can be various levels of T-wave variability, and that more than a binary decision occurs. For example, there can be two, three or more (e.g., infinite) possible degrees of T-wave variability. Additional details of how to determine the absence, presence or degree of T-wave variability from an IEGM signals are discussed in more detail below.

At step 412, there is a discrimination between VT and SVT based on the results of step 410, and more specifically, based on the detected absence, presence or degree of T-wave variability in the portion of the IEGM signal indicative of cardiac activity leading up to the onset of the detected tachycardia.

It is believed that the presence of T-wave variability prior to the onset of a tachycardia is indicative of VT, where the absence of T-wave variability prior to the onset of a tachycardia is indicative of SVT. Additionally, it is believed that the degree of T-wave variability (if that is what is being monitored) will increase prior to the onset of VT, but will stay relatively the same prior to the onset of SVT. Accordingly, in accordance with specific embodiments of the present invention, T-wave variability analysis is used in the discrimination between VT and SVT.

More specifically, at step 412, if T-wave variability was present or a degree of T-wave variability exceeded a specified threshold, there can be a determination that the portion of the IEGM signal is indicative of VT. In contrast, if T-wave variability was absent or a degree of T-wave variability did not exceed a specified threshold, there can be a determination at step 412 that the portion of the IEGM signal is indicative of SVT.

T-wave variability analysis can be used as the sole arrhythmia discrimination qualifier, or more likely, as one of a few or many discrimination qualifiers, some of which were discussed above, including morphology, sudden onset, interval stability (also known as rate stability), and T-wave alternans analysis. In other words, the above described T-wave variability analysis can be used to independently discriminate between VT and SVT, or can be used together with other techniques for discrimination between VT and SVT. For example, the above described embodiments can be used to supplement (e.g., to increase the confidence level of) arrhythmia discrimination performed using some other technique(s), including but not limited to interval stability, sudden onset, morphology, and/or T-wave alternans analysis discrimination techniques. Alternatively, some other technique(s) can be used to supplement the arrhythmia discrimination performed using the T-wave variability analysis described above. It is also possible that the T-wave variability analysis be used in one or more branch of rate branch algorithm, examples of which are described above. Some exemplary details of interval stability, sudden onset and morphology discrimination techniques were provided above, for completeness. Also, discrimination techniques that rely on T-wave variability were also described above.

In accordance with specific embodiments, the implantable system can substantially continually monitoring for a tachycardia, and substantially continually monitoring for an absence, presence or degree of T-wave variability while monitoring for a tachycardia. This way, when a tachycardia is detected, there can be a substantially immediate determination of the absence, presence or degree of T-wave variability in a portion of an IEGM signal indicative of cardiac activity leading up to the onset of the detected tachycardia.

In an alternative embodiments, the detection of a tachycardia by the implantable system can trigger the determination of the absence, presence or degree of T-wave variability. More specifically, a portion of an IEGM can be repeatedly stored in a buffer (e.g., buffer 295). Then, when a tachycardia is detected, the contents of the buffer can be froze, so that the contents of the buffer includes a portion of the IEGM signal indicative of cardiac activity leading up to the onset of the detected tachycardia. The implantable system can then determine, based on the contents of the buffer, the presence, absence or degree of T-wave variability in the portion of the IEGM signal indicative of cardiac activity leading up to the onset of the detected tachycardia. Another way that the implantable system can use a buffer to determine the presence, absence or degree of T-wave variability leading up to the onset of the detected tachycardia is as follows. T-wave metrics can be determined in real or near real time, and such metrics can be stored in a buffer. Then, when a tachycardia is detected, the contents of the buffer can be froze, so that the contents of the buffer includes T-wave metrics corresponding to cardiac activity leading up to the onset of the detected tachycardia (rather than the buffer storing raw IEGM data). The implantable system can then determine, based on the contents of the buffer, the presence, absence or degree of T-wave variability leading up to the onset of the detected tachycardia.

To monitor for T-wave variability, T-wave metrics can be measured to determined whether variability in T-waves exist, and/or to what extent. In other words, T-wave variability can be a measure of variability of one or more T-wave metric. Exemplary T-wave metrics, of which a variability can be calculated, include, but are not limited to: maximum amplitude of T-wave, minimum amplitude of T-wave, peak-to-peak amplitude of T-wave, location of maximum amplitude of T-wave, location of minimum amplitude of T-wave, area under T-wave, slope of T-wave, T-wave amplitude dispersion, T-wave centroid, QT interval, corrected QT interval, amplitude of ST segment, T-wave frequency content, and T-wave frequency spread. Another exemplary T-wave metric (whose variability can be determined and monitored) is QT max–QT end. There are various techniques that are known for identifying T-waves, thereby enabling measurement of the above mentioned T-wave metrics. Some exemplary techniques for detecting T-waves are disclosed in U.S. patent application Ser. No. 10/979,833, entitled "Systems and Methods for Automatically Setting Refractory and Blanking Periods," (Snell and Bharmi) filed Nov. 1, 2004 which is incorporated herein by reference. Some additional exemplary techniques for detecting T-waves are disclosed in U.S. Pat. No. 5,782,887 (van Krieken et al) and U.S. Pat. No. 6,836,682 (Van Dam), which are incorporated herein by reference. Use of alternative techniques for detecting T waves are within are also within the scope of the present invention.

For each of the above T-wave metrics, actual, absolute, normalized (e.g., to heart rate and/or R-wave amplitude), or otherwise adjusted values can be used. The monitored T-wave variability can be, e.g., a variability of any one of the above T-wave metrics, or a weighted average of the variability of multiple ones of the above T-wave metrics. In addition, or instead of using the above T-wave metrics, T-wave variability can be of isochoric points of the T-wave. T-wave variability may also be or include a measure of the variability of a magnitude of T-wave alternans. In other words, magnitudes of T-wave alternans can be a T-wave metric for which a measure of variability is determined.

T-wave variability can be determined by calculating a standard deviation, a pseudo random deviation, root mean-square differences, a range, a interquartile range, a mean difference, a median absolute deviation, an average absolute deviation, etc., of any of the above mentioned T-wave metrics, or combinations thereof, or other T-wave metrics. These are just a few examples, which are not meant to be limiting. Also, it is noted that most any known technique for determining heart rate variability (HRV), including but not limited to time domain, frequency domain, and non-linear techniques, can be used to determine T-wave variability by using measures of T-wave metrics in place of measures of RR intervals.

In specific embodiments, a T-wave variability can be determined at implant, or at some other time when the patient is known to not be experiencing a tachycardia. This can be considered the patient's baseline T-wave variability.

When T-wave variability is monitored at step 410, this can include determining a value of T-wave variability, comparing the value of T-wave variability to one or more threshold, and/or comparing a difference between the value of T-wave variability and the baseline T-wave variability to a corresponding threshold. The baseline T-wave variability may also be updated from time to time, but preferably should be determined based on T-wave metrics obtained when the patient is not experiencing episodes of a disorder.

FIG. 5 is a high level flow diagram that is used to summarize specific embodiments of the present invention that relate discriminating between VT and SVT based on cardiac electrical stability leading up to the onset of a tachycardia. Cardiac electrical stability can be determined based in the absence, presence or degree of T-wave alternans in a portion of an IEGM signal indicative of cardiac activity leading up to the onset of a detected tachycardia. Alternatively, or additionally, cardiac electrical stability can be determined based in the absence, presence or degree of T-wave variability in a portion of an IEGM signal indicative of cardiac activity leading up to the onset of a detected tachycardia. Alternative or additional techniques for determining cardiac electrical stability can be used, and are also within the scope of the present invention.

Steps 302-306 and 314-320 in FIG. 5 are the same as those steps in FIG. 3, and thus those steps need not be discussed again. Block 508 indicates that discriminating between VT and SVT is being based on cardiac electrical stability, as will be described below with reference to steps 510 and 512.

Referring to FIG. 5, at step 510, there is a determination of the cardiac electrical stability leading up to the onset of a detected tachycardia. More specifically, there can be a binary determination, at step 510, of whether cardiac electrical stability is above or below a specified threshold. This determination can take place by determining a magnitude of T-wave alternans and/or variability of T-waves (in a portion of an IEGM signal indicative of cardiac activity leading up to the onset of a detected tachycardia), and comparing the determined magnitude(s) to a corresponding threshold(s). If the threshold(s) is (/are) not exceeded, then there can be a determination that the cardiac electrical stability is stable. If the threshold(s) is (/are) reached or exceeded, then there can be a determination that the cardiac electrical stability is instable.

Alternatively, at step 510, a degree of cardiac electrical stability can be determined, meaning that there can be various levels of cardiac electrical stability, and that it is more than a binary decision.

At step 512, there is a discrimination between VT and SVT based on the results of step 510, and more specifically, based on the detected cardiac electrical stability leading up to the onset of the detected tachycardia, e.g., as determined based on the portion of the IEGM signal indicative of cardiac activity leading up to the onset of the detected tachycardia.

It is believed that cardiac electrical instability prior to the onset of a tachycardia is indicative of VT, where the cardiac electrical stability prior to the onset of a tachycardia is indicative of SVT. Additionally, it is believed that the degree of cardiac electrical instability (if that is what is being monitored) will increase prior to the onset of VT, but that stability will stay relatively the same prior to the onset of SVT.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use by an implantable system, a method for discriminating between ventricular tachycardia (VT) and supraventricular tachycardia (SVT), comprising:
    (a) detecting an absence, presence or degree of T-wave alternans leading up to the onset of a detected tachycardia; and
    (b) discriminating between VT and SVT based on the detected absence, presence or degree of T-wave alternans.

2. The method of claim 1, wherein:
   step (a) comprises detecting an absence, presence or degree of T-wave alternans in a portion of an IEGM signal indicative of cardiac activity leading up to the onset of a detected tachycardia; and
   step (b) comprises discriminating between VT and SVT based on the detected absence, presence or degree of T-wave alternans in the portion of the IEGM.

3. The method of claim 2, wherein step (b) includes, when discriminating between VT and SVT:
   if T-wave alternans were present or the detected degree of T-wave alternans exceeded a specified threshold, determining that the portion of the IEGM signal is indicative of VT; and
   if T-wave alternans were absent or the detected degree of T-wave alternans did not exceed a specified threshold, determining that the portion of the IEGM signal is indicative of SVT.

4. The method of claim 1, further comprising monitoring for a tachycardia, and performing steps (a) and (b) in response to detecting a tachycardia.

5. The method of claim 1, further comprising monitoring for a tachycardia, and performing steps (a) and (b) in response to detecting a tachycardia where the ventricular rate exceeds a VT threshold but does not exceed a ventricular fibrillation (VF) threshold.

6. The method of claim 1, further comprising monitoring for a tachycardia, and performing steps (a) and (b) in response to detecting a tachycardia where the ventricular rate is less than or substantially equal to the atrial rate.

7. The method of claim 1, wherein:
   step (a) comprises detecting an absence or presence of T-wave alternans in a portion of an IEGM signal indicative of cardiac activity leading up to the onset of a detected tachycardia; and
   step (b) comprises
       determining that the portion of the IEGM signal is indicative of VT, if T-wave alternans were present in the portion of the IEGM signal, and
       determining that the portion of the IEGM signal is indicative of SVT, if T-wave alternans were absent in the portion of the IEGM signal.

8. The method of claim 1, wherein:
   step (a) comprises detecting a degree of T-wave alternans in a portion of an IEGM signal indicative of cardiac activity leading up to the onset of a detected tachycardia; and
   step (b) comprises
       determining that the portion of the IEGM signal is indicative of VT, if the detected degree of T-wave alternans exceeded a specified threshold, and
       determining that the portion of the IEGM signal is indicative of SVT, if the detected degree of T-wave alternans did not exceed a specified threshold.

9. The method of claim 1, further comprising:
   substantially continually monitoring for a tachycardia; and
   substantially continually monitoring for an absence, presence or degree of T-wave alternans while monitoring for a tachycardia, so that when a tachycardia is detected, there can be a substantially immediate determination of the absence, presence or degree of T-wave alternans leading up to the onset of the detected tachycardia.

10. The method of claim 1, further comprising:
    repeatedly storing a portion of an IEGM in a buffer; and
    when a tachycardia is detected
        freezing contents of the buffer so that the contents of the buffer includes the portion of the IEGM signal indicative of cardiac activity leading up to the onset of the detected tachycardia; and
        determining, based on the contents of the buffer, the presence, absence or degree of T-wave alternans in the portion of the IEGM signal indicative of cardiac activity leading up to the onset of the detected tachycardia.

11. The method of claim 1, further comprising:
    repeatedly storing T-wave metrics in a buffer; and
    when a tachycardia is detected
    freezing contents of the buffer so that the contents of the buffer includes the T-wave metrics leading up to the onset of the detected tachycardia; and
    determining, based on the contents of the buffer, the presence, absence or degree of T-wave alternans leading up to the onset of the detected tachycardia.

12. The method of claim 1, further comprising:
    (c) delivering a first type of cardiac therapy if it is determined at step (b) that the detected tachycardia is VT; and
    (d) delivering a second type of cardiac therapy, or no cardiac therapy, if it is determined at step (b) that the detected tachycardia is SVT.

13. An implantable system capable of discriminating between ventricular tachycardia (VT) and supraventricular tachycardia (SVT), comprising:
    an alternans monitor to monitor an IECM for an absence, presence or degree of T-wave alternans; and
    an arrhythmia discriminator to discriminate between VT and SVT based on the absence, presence or degree of T-wave alternans leading up to the onset of a detected tachycardia, as determined by the alternans monitor.

14. The implantable system of claim 13, further comprising:
    an arrhythmia monitor to monitor for a tachycardia.

15. For use by an implantable system, a method for discriminating between ventricular tachycardia (VT) and supraventricular tachycardia (SVT), comprising:
    (a) detecting an absence, presence or degree of T-wave variability leading up to the onset of a detected tachycardia; and
    (b) discriminating between VT and SVT based on the detected absence, presence or degree of T-wave variability.

16. The method of claim 15, wherein:
step (a) comprises detecting an absence, presence or degree of T-wave variability in a portion of an IEGM signal indicative of cardiac activity leading up to the onset of a detected tachycardia; and
step (b) comprises discriminating between VT and SVT based on the detected absence, presence or degree of T-wave variability in the portion of the IEGM.

17. The method of claim 16, wherein step (b) includes, when discriminating between VT and SVT:
if T-wave variability was present or the detected degree of T-wave variability exceeded a specified threshold, determining that the portion of the IEGM signal is indicative of VT; and
if T-wave variability was absent or the detected degree of T-wave variability did not exceed a specified threshold, determining that the portion of the IEGM signal is indicative of SVT.

18. The method of claim 15, further comprising:
substantially continually monitoring for a tachycardia; and
substantially continually monitoring for an absence, presence or degree of T-wave variability while monitoring for a tachycardia, so that when a tachycardia is detected, there can be a substantially immediate determination of the absence, presence or degree of T-wave variability leading up to the onset of the detected tachycardia.

19. The method of claim 15, further comprising:
repeatedly storing a portion of an IEGM and/or T-wave metrics in a buffer; and
when a tachycardia is detected
freezing contents of the buffer so that the contents of the buffer are indicative of cardiac activity leading up to the onset of the detected tachycardia; and
determining, based on the contents of the buffer, the presence, absence or degree of T-wave variability leading up to the onset of the detected tachycardia.

20. The method of claim 15, further comprising:
(c) delivering a first type of cardiac therapy if it is determined at step (b) that the detected tachycardia is VT; and
(d) delivering a second type of cardiac therapy, or no cardiac therapy, if it is determined at step (b) that the detected tachycardia is SVT.

21. An implantable system capable of discriminating between ventricular tachycardia (VT) and supraventricular tachycardia (SVT), comprising:
a variability monitor to monitor an IEGM for T-wave variability; and
an arrhythmia discriminator to discriminate between VT and SVT based on an absence, presence or degree of T-wave variability leading up to the onset of a detected tachycardia, as determined by the variability monitor.

22. The implantable system of claim 21, further comprising:
an arrhythmia monitor to monitor for a tachycardia.

23. For use by an implantable system, a method for discriminating between ventricular tachycardia (VT) and supraventricular tachycardia (SVT), comprising:
(a) determining the cardiac electrical stability leading up to the onset of a detected tachycardia; and
(b) discriminating between VT and SVT based on the cardiac electrical stability leading up to the onset of the detected tachycardia.

24. The method of claim 23, wherein step (b) includes, when discriminating between VT and SVT:
if the cardiac electrical stability leading up to the onset of the detected tachycardia is determined to be instable, determining that the cardiac electrical stability is indicative of VT; and
if the cardiac electrical stability leading up to the onset of the detected tachycardia is determined to be stable, determining that the cardiac electrical stability is indicative of SVT.

25. The method of claim 23, further comprising:
repeatedly storing a portion of an IEGM and/or metrics of the IEGM in a buffer; and
when a tachycardia is detected
freezing contents of the buffer so that the contents of the buffer are indicative of cardiac activity leading up to the onset of the detected tachycardia; and
determining, based on the contents of the buffer, the cardiac electrical stability leading up to the onset of the detected tachycardia.

* * * * *